(12) United States Patent
Stamberg (10) Patent No.: US 8,992,817 B2
(45) Date of Patent: Mar. 31, 2015

(54) PROCESS OF MAKING A MEDICAL BALLOON

(71) Applicant: Abbott Cardiovascular Systems Inc., Santa Clara, CA (US)

(72) Inventor: Barbara E. Stamberg, San Jose, CA (US)

(73) Assignee: Abbott Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 13/709,765

(22) Filed: Dec. 10, 2012

(65) Prior Publication Data

US 2014/0163601 A1    Jun. 12, 2014

(51) Int. Cl.
  *B32B 1/08* (2006.01)
  *A61B 17/12* (2006.01)
  *D01D 5/00* (2006.01)
  *A61M 25/10* (2013.01)
  *A61L 29/04* (2006.01)
  *A61L 29/14* (2006.01)
  *A61L 29/16* (2006.01)
  *A61B 17/00* (2006.01)

(52) U.S. Cl.
  CPC ........ *A61B 17/12109* (2013.01); *D01D 5/0023* (2013.01); *A61B 17/00008* (2013.01); *A61B 17/12031* (2013.01); *A61B 17/12045* (2013.01); *A61B 17/12136* (2013.01); *A61B 2017/00526* (2013.01); *A61B 2017/00889* (2013.01); *A61B 2017/00893* (2013.01); *A61B 2017/12127* (2013.01); *A61M 25/10* (2013.01); *A61M 25/1029* (2013.01); *A61M 2025/105* (2013.01); *A61L 29/04* (2013.01); *A61L 29/14* (2013.01);

*A61L 29/148* (2013.01); *A61L 29/16* (2013.01); *A61L 2400/12* (2013.01); *D01D 5/0007* (2013.01)
USPC .................. 264/465; 264/171.26; 264/171.29; 264/211.1

(58) Field of Classification Search
USPC ................ 264/10, 211.1, 464, 465, 466, 484, 264/171.1, 171.26, 171.29, 255, 312
See application file for complete search history.

(56) References Cited

U.S. PATENT DOCUMENTS

| | | |
|---|---|---|
| 5,458,568 A | 10/1995 | Racchini |
| 6,129,706 A | 10/2000 | Janacek |
| 6,585,926 B1 | 7/2003 | Mirzaee |
| 7,273,471 B1 | 9/2007 | Wang |
| 7,335,184 B2 | 2/2008 | Laguna |
| 8,663,541 B2* | 3/2014 | Chun et al. ............... 264/465 |
| 2004/0009600 A1* | 1/2004 | Bowlin et al. ........... 435/395 |
| 2004/0053553 A1* | 3/2004 | Dubson et al. ........... 442/340 |
| 2006/0204441 A1* | 9/2006 | Atala et al. ............... 424/9.6 |

(Continued)

*Primary Examiner* — Leo B Tentoni
(74) *Attorney, Agent, or Firm* — Lisa A. Chiarini; Walter M. Egbert, III; Hughes Hubbard & Reed LLP (57) ABSTRACT

The disclosed subject matter describes systems and methods of electrospinning a fiber for a variety of applications. An exemplary embodiment includes a medical device application for delivering a therapeutic agent, such as a sclerosing agent, to the walls of a blood vessel to perform sclerotherapy. A method of fabricating a medical balloon comprises charging a polymer material with an electric voltage, dispensing the charged polymeric material through a nozzle, collecting the charged polymeric material on a grounded mandrel, wherein the mandrel includes a tubular body having a plurality of openings extending through the tubular body, and forming an electrospun medical balloon defined by a body having a varied thickness.

9 Claims, 7 Drawing Sheets

(56) References Cited

U.S. PATENT DOCUMENTS

| | | |
|---|---|---|
| 2006/0271154 A1 | 11/2006 | Woodall |
| 2007/0213671 A1 | 9/2007 | Hiatt |
| 2010/0072674 A1* | 3/2010 | Takahashi et al. ............ 264/465 |
| 2011/0236974 A1* | 9/2011 | Ogle et al. ................ 264/465 X |
| 2013/0178949 A1* | 7/2013 | Bowlin et al. .............. 623/23.72 |

* cited by examiner

PROCESS OF MAKING A MEDICAL BALLOON

FIELD

The disclosed subject matter relates to electrospinning methods and apparatus. The methods and apparatus disclosed herein are applicable in a wide variety of industries including filtration, textiles, photonic, medical, energy and aerospace. One exemplary application of the disclosed subject matter is the treatment of blood vessels using a therapeutic agent. More particularly, the disclosed subject matter relates to a medical device having a porous e-spun balloon which can be employed as a sclerotherapy device having a balloon with varied thickness across a length thereof and is configured to deliver sclerosing agent to a vein of a subject.

BACKGROUND

Blood vessels that have become enlarged and tortuous over a period of time are generally known as "varicose veins." Most commonly, varicose veins occur in veins of the legs, and in particular, are most common in the superficial veins of the legs, although they can occur elsewhere. Varicose veins are caused when the leaflets of valves in the blood vessel no longer close properly, thereby allowing for retrograde flow and pooling of blood within the vein. Varicose veins are often painful and can produce ankle swelling, skin discoloration, dermatitis or venous eczema, cramps, and skin tightness around the affected region. In severe cases of varicose veins, complications may occur. For example, the varicose veins may become very painful and hinder a person's ability to walk. Further, skin conditions associated with varicose veins may also predispose a person to skin loss. Development of serious conditions like blood clots, carcinoma, or sarcoma, may also occur.

The traditional surgical treatment for varicose veins is "vein stripping" during which the affected vein is removed. Other non-surgical treatments include wearing elastic stockings, elevating the legs, and exercising. Another treatment is sclerotherapy.

Sclerotherapy is a treatment during which a sclerosing agent is injected into the varicose vein to cause shrinking of the vein. In order for sclerotherapy to be effective, it is necessary to evenly dispense the sclerosing agent throughout the wall of the vein without using toxic levels of the sclerosing agent. This is not particularly difficult for the smaller veins. However, it is quite difficult or nearly impossible in larger veins. When a larger vein is injected with a sclerosing agent, the sclerosing agent is quickly diluted by the large volume of blood in the vein. As a result, the vein is sclerosed only in the region of the injection. If the procedure is continued, and the injections are far apart, the vein can become disfigured. The problem cannot be cured by injecting a more potent solution of sclerosing agent, because the sclerosing agent may become toxic at such a concentration. Therefore, a need exists for a system that is capable of delivering a sclerosing agent to the varicose vein walls that prevents the dilution of the sclerosing agent into the blood and more evenly delivers the sclerosing agent to the wall of the vessel.

SUMMARY

The purpose and advantages of the disclosed subject matter will be set forth in and apparent from the description that follows, as well as will be learned by practice of the disclosed subject matter. Additional advantages of the disclosed subject matter will be realized and attained by the methods and systems particularly pointed out in the written description and claims hereof, as well as from the appended drawings.

The presently disclosed subject matter provides methods and devices for fabricating a medical device, and in particular to methods and devices for localized delivery of a therapeutic agent, for example for use in sclerotherapy treatment. Although the exemplary embodiments described herein relate primary to a catheter for treating varicose veins by locally delivering a sclerosing agent, one of ordinary skill in the art would appreciate that the catheter and medical balloon described and the methods and techniques can be used for the local delivery of any therapeutic agent within a blood vessel of a patient. As such, the following description and claims should not be limited to a sclerotherapy device and methods.

In one embodiment, the method includes fabricating a medical balloon by electrospinning a polymer material associated with a mandrel having a plurality of apertures.

The openings on the mandrel may be of any desired shape. For example, the openings of the mandrel may be circular and/or of uniform size. Additionally, the size of the openings may be different depending upon the intended use of the medical device and/or therapeutic agent employed. For example, the openings may be approximately 1 mm in diameter if the medical device is being used to perform sclerotherapy.

The spacing of the openings on the mandrel may also be varied depending upon the intended use of the medical device and/or therapeutic agent employed. In some embodiments, the openings are disposed uniformly along the entire length of the mandrel. In other embodiments, the openings are disposed only at the ends of the mandrel and/or the mid-section of the mandrel, or with a gradual variance in the density of holes disposed along a length of the mandrel.

Many methods may be utilized for forming the medical device on the mandrel using techniques and materials that are well known in the art. For example, the depositing step may include electrospinning a fluid through a nozzle onto the mandrel. The electrospun polymer forms polymeric fibers on the mandrel to form a tubular fibrous layer having a varied thickness. Other methods of forming the medical device include melt-blowing and/or using a spunbonding process.

In other embodiments, a method of fabricating a medical device is provided. The method comprises electrospinning a polymer fluid onto a mandrel, the mandrel having a tubular body and a plurality of openings extending through the tubular body, and forming a fibrous structure having a body defined by a wall, and further wherein the wall has a varied thickness. The varied thickness in the wall includes a thin wall thickness and a thicker wall thickness along sections of the fibrous structure.

A method of fabricating a medical balloon is provided in which a polymer is charged with an electric voltage. The charged polymer is dispensed through a nozzle or other electrospinning element and collected on a grounded mandrel. The mandrel includes a tubular body having a plurality of openings extending through the tubular body and an electrospun medical balloon defined by a body having a varied thickness is formed. The varied thickness of the balloon includes porous sections and non-porous sections.

The method can include rotating the nozzle while dispensing the polymeric material, rotating the mandrel, or rotating both components. The electric charge applied to the polymeric material can be between about 2000 to 400,000 V/m. Although it depends on the application. The mandrel is generally positioned about 0.5 cm to about 25 cm from the nozzle, for some applications and accuracy, it can be positioned in close proximity the nozzle.

In one exemplary embodiment of the disclosed subject matter, a method for treating a varicose vein is described. The method includes occluding a section of a varicose vein, and then introducing a catheter having an e-spun polymeric balloon including a body having a varied thickness defined by porous and non-porous or semi-porous sections. A sclerosing agent, such as ethanol, is dispensed through the porous sections of the e-spun polymeric balloon to treat a portion of the vein. The e-spun balloon can be formed from many various polymers. In some instances, it can be formed of biodegradable material. In one embodiment, the method can further include inflating the e-spun polymeric balloon to a pressure sufficient to contact and apply a force to the wall of the vein. In this manner, the pressure from the balloon against the wall of the vein can massage or further facilitate treatment of the vein with the sclerosing agent. Thus, the force can be applied to the wall of the vein after the sclerosing agent is dispensed from the e-spun polymeric balloon.

In accordance with another aspect, a catheter device is described. The catheter includes an elongated catheter shaft having a proximal portion and a distal portion. The shaft has at least one inflation lumen disposed between the proximal portion and distal portion and in fluid communication with an expandable member. The expandable members include a first expandable member disposed at the distal portion of the catheter shaft, and a second expandable member having an e-spun polymeric material body having a varied thickness including porous and non-porous sections. The second expandable member disposed on the catheter proximal to the first expandable member. The first expandable member is an occlusion balloon, and the second expandable member has porous sections configured to dispense a beneficial agent.

In another aspect, a system is provided for fabricating an e-spun polymeric member, such as a stent or a balloon. The system includes a mandrel having a tubular body and a plurality of openings extending through the tubular body, and an electrospinning element capable of being positioned in close proximity to the mandrel. The openings in the mandrel are between 1 micron and 1 cm. The mandrel can be removably attached to a holder. The electrospinning element is capable of being positioned between 0.5 cm to about 25 cm from the mandrel. In some embodiments, the system further comprises an electrifiable reservoir to hold a polymer fluid or melt and associated with the electrospinning element. The electrospinning element can include a nozzle having a Taylor cone.

BRIEF DESCRIPTION OF THE DRAWINGS

A detailed description of various aspects, features, and embodiments of the subject matter described herein is provided with reference to the accompanying drawings, which are briefly described below. The drawings are illustrative and are not necessarily drawn to scale, with some components and features being exaggerated for clarity. The drawings illustrate various aspects and features of the present subject matter and may illustrate one or more embodiment(s) or example(s) of the present subject matter in whole or in part.

DETAILED DESCRIPTION OF EXEMPLARY EMBODIMENTS

It is understood that the subject matter described herein is not limited to particular embodiments described, and as such may, of course, vary. It is also understood that the terminology used herein is for the purpose of describing particular embodiments only, and is not intended to be limiting, since the scope of the present subject matter is limited only by the appended claims. Where a range of values is provided, it is understood that each intervening value between the upper and lower limit of that range and any other stated or intervening value in that stated range, is encompassed within the disclosed subject matter.

Catheter Body

Figure 1:
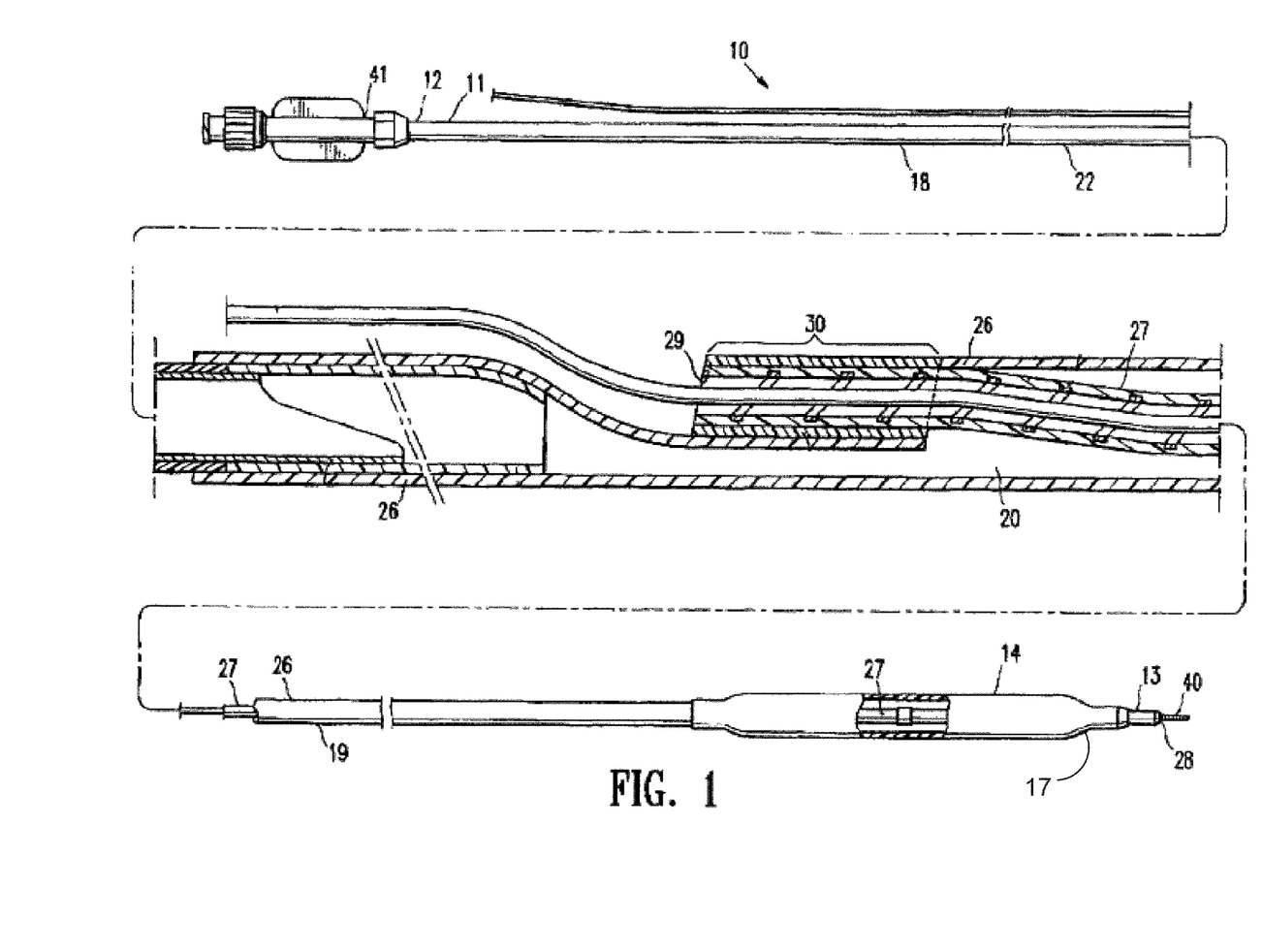
FIG. 1 is a schematic view of a rapid exchange catheter having an expandable member constructed of a plurality of fibers in accordance with the disclosed subject matter.
Figure 2A:
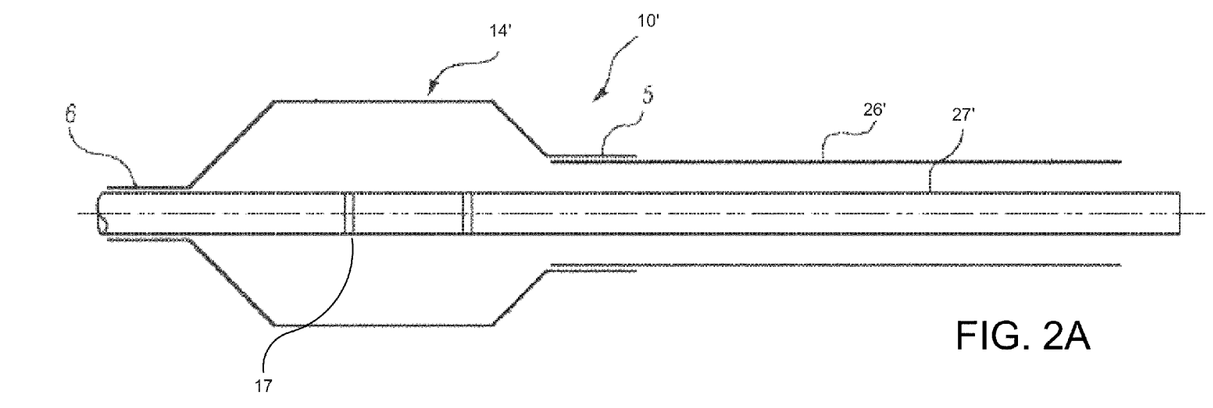
FIG. 2A is a schematic cross-sectional view of an over-the-wire catheter having a coaxial arrangement and an expandable member constructed of a plurality of fibers in accordance with the disclosed subject matter.
Figure 2B:
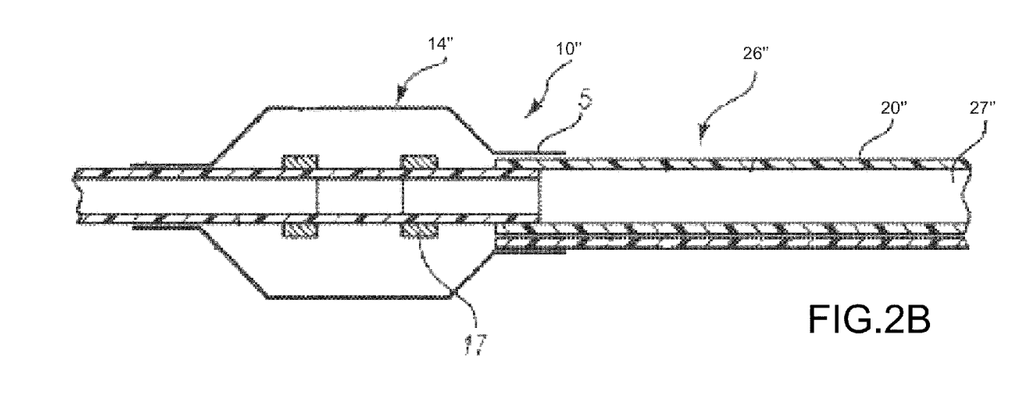
FIG. 2B is a schematic cross-sectional view of an over-the-wire catheter having a side-by-side arrangement and an expandable member constructed of a plurality of fibers in accordance with the disclosed subject matter

In one aspect of the disclosed subject matter, a catheter having an e-spun polymer balloon is provided, as shown schematically in FIG. 1 and FIG. 2. Referring to FIG. 1, the catheter 10 generally includes an elongated catheter shaft 11 having a proximal end 12 and having a distal end 13 and an e-spun polymeric member 14 located proximate to the distal end of the catheter shaft 11. The catheter shaft 11 includes an inner tubular member 27, defining a guide wire lumen, and an inflation lumen 20.

In one embodiment, a proximal shaft section 18 comprises a proximal tubular member 22 defining a proximal portion of the inflation lumen 20. In the embodiment illustrated in FIG. 1, the distal end of the proximal tubular member 18 tapers distally to a smaller transverse dimension. A distal shaft section 19 comprises an outer tubular member 26 defining a distal portion of the inflation lumen 20 and an inner tubular member 27 which defines a guidewire lumen that is in fluid communication with a guidewire distal port 28 at the distal end of the catheter, and a guidewire proximal port 29 at the proximal end of the inner tubular member 27. The e-spun polymeric member 14 has a proximal end sealingly secured to the distal end of outer tubular member 26 and a distal end sealingly secured to the distal end of inner tubular member 27, so that its interior is in fluid communication with inflation lumen 20. An adapter 41 at the proximal end of the catheter provides access to the inflation lumen 20.

In one embodiment, a rapid exchange transition section is defined at the guidewire proximal port 29 where the catheter shaft transitions between a single lumen proximal shaft section and a multi-lumen distal shaft section to define a rapid exchange catheter. The inner tubular member 27 extends through an opening in a sidewall of the outer tubular member 26. A proximal portion 30 of the inner tubular member 27 disposed proximate to a sidewall inlet and is secured to the outer tubular member 26. The inner tubular member proximal portion 30 defines a portion of the guidewire lumen extending proximally of the sidewall inlet. Distal to the proximal portion 30, the inner tubular member 27 transitions to a generally coaxial configuration within the inflation lumen 20 defined by the outer tubular member 26. Although in the illustrated embodiment the inner tubular member 27 is coaxial with a distal portion of the outer tubular member 26, a variety of suitable configurations may be used including a non-coaxial configuration, for example, a side-by-side configuration in which all or part of the length of the inner tubular member is secured to the catheter shaft and is exterior to the inflation lumen.

In another embodiment, the catheter 10' is an over-the-wire (OTW) catheter. In accordance with this embodiment, the guide wire lumen can extend from the proximal end of the catheter to the distal end of the catheter in a coaxial arrangement. As shown in FIG. 2A, the proximal section 5 of the e-spun polymeric member 14' is sealed to the distal end 6 of the outer tubular member 26' and the distal end 6 of the e-spun polymeric member 14' is sealed around the outside of the inner tubular member 27' extending through the center of the balloon. The proximal and distal seals of the balloon allow for fluid pressurization and balloon inflation from the proximal hub of the catheter.

In yet another embodiment, as schematically shown in FIG. 2B, the over-the-wire catheter 10" can have a side-by-side arrangement. In this embodiment, the inner tubular member 27" defining the guide wire lumen is parallel to and exterior to the outer tubular member 26" defining the inflation lumen 20".

The distal end of catheter embodiments may be advanced to a desired region of a patient's body lumen in a conventional manner, e-spun polymeric member 14 inflated to perform a procedure. Then, the e-spun polymeric member may be deflated and the catheter repositioned or withdrawn from the body lumen.

Materials suitable for use for forming the tubular members of the catheter include, but are not limited to, Polyurethanes (PU), such as Tecoflex, Pellethene, Bionate, corethane, Elasteon, and blends thereof; Polyethylenes (PE), such as PET, PBT, PVDF, Teflon, ETFE, and blends thereof, Polyolefins, such as HDPE, PE, LDPE, LLDPE, Polypropylene, and blends thereof, Polyimides; Polyamides; all classes of Nylons, such as Nylon 11, Nylon 12, Nylon 6,6, Nylon 6, Nylon 7,11, Nylon 11,12, and blends thereof); block copolymers; PEBA-types polymers, such as ELY, PEBAX, Ubesta, and blends thereof, and biodegradable polymers.

Suitable materials also include blends of the above mentioned materials as well as any composite materials, like dual-layers, tri-layers and multi-layers thereof. For example, catheter shaft 11 may be produced from a tube comprising an outer layer made of Nylon and an inner layer made of a lubricious material such as polyethylene or PTFE. A metallic or nonmetallic braiding may also be included within or between layers of the catheter members, in particular the proximal section of the catheter body.

In some embodiments, the length of the catheter 10, 10', 10" is generally about 108 to about 200 centimeters, preferably about 137 to about 145 centimeters. The outer tubular member distal section can have an outer diameter (OD) of about 0.028 to about 0.036 inch (0.70-0.91 mm), and an inner diameter (ID) of about 0.024 to about 0.035 inch (0.60-0.89 mm), and the outer tubular member proximal section can have an OD of about 0.017 to about 0.034 inch (0.43-0.87 mm), and an inner diameter (ID) of about 0.012 to about 0.022 inch (0.30-0.56 mm). The inner tubular member 15 can have an OD of about 0.017 to about 0.026 inch (0.43-0.66 mm), and an ID of about 0.015 to about 0.018 inch (0.38-0.46 mm) depending on the diameter of the guidewire to be used with the catheter. The balloon 19 can have a length of about 8 mm to about 40 mm, and an inflated working diameter of about 1.5 mm to about 5 mm.

In some embodiments, the catheter 10, 10', 10" can include one or more radiopaque markers 17, as illustrated in FIGS. 1, 2A, and 2B. The radiopaque markers can be included on the inner tubular member under the e-spun polymeric member 14, outer tubular shaft 26 or the distal end of the catheter, and various other suitable locations on the catheter. The radiopaque marker can be polymeric or metallic and provides for visualizing a distal end section of the catheter shaft to facilitate accurately positioning the catheter. In one embodiment, the polymeric radiopaque marker is a blend of polymeric and radiopaque materials, which provides a flexible, bright (under fluoroscopy) marker. The polymeric radiopaque marker is preferably secured to the catheter shaft to provide a smooth transition in stiffness at the catheter distal tip which may improve introduction of the catheter through the vasculature. In one embodiment, the marker is a ring applied to the distal section or distal end of the catheter shaft.

The distal end of catheter may be advanced—to a desired region of a patient's body lumen in a conventional manner and e-spun polymeric member 14 inflated to perform a procedure such as sclerotherapy of a varicose region, and catheter 100 withdrawn or repositioned for another procedure.

Balloon

In another aspect of the disclosed subject matter, a medical balloon is formed from e-spun polymeric material. The term "e-spun" and "electro-spun" as used herein refers to a member made by an electrospinning process. The terms e-spun and electrospun should be understood to be interchangeable. The term "electrospinning" refers to use of an electrical charge to draw very fine (typically on the micro or nano scale) fibers from a liquid. Thus, in another aspect of the disclosed subject matter, methods are provided for forming the e-spun polymeric member 14. In electrospinning molecules or crystals are oriented such that they have high tensile strength (e.g. Young's modulus of 19.3 GPa). Electrospun fibers have a cylindrical structure and controllable porosity, and allow for surface-area to volume or mass ratios up to 100000 times higher than conventionally spun fibers.

Figure 3:
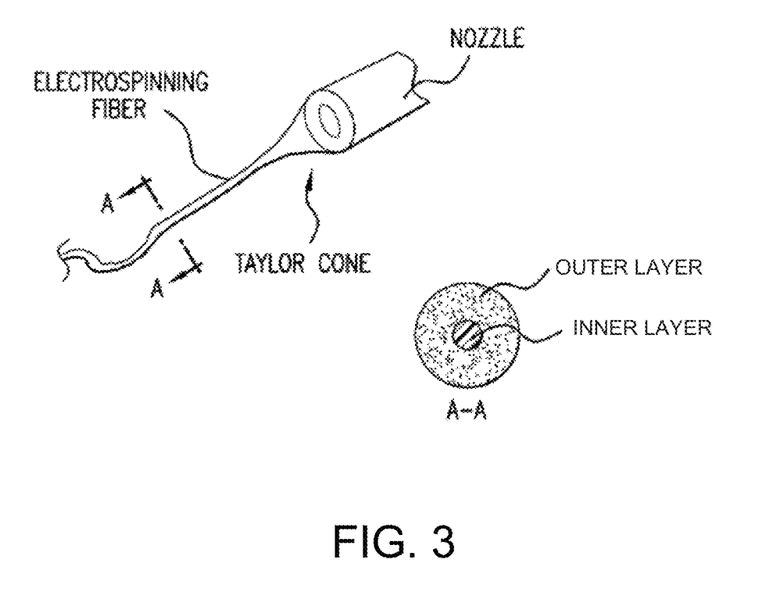
FIG. 3 and FIG. 4 are schematic drawings of an exemplary electrospinning process used to form the expandable member of the disclosed subject matter.
Figure 4:
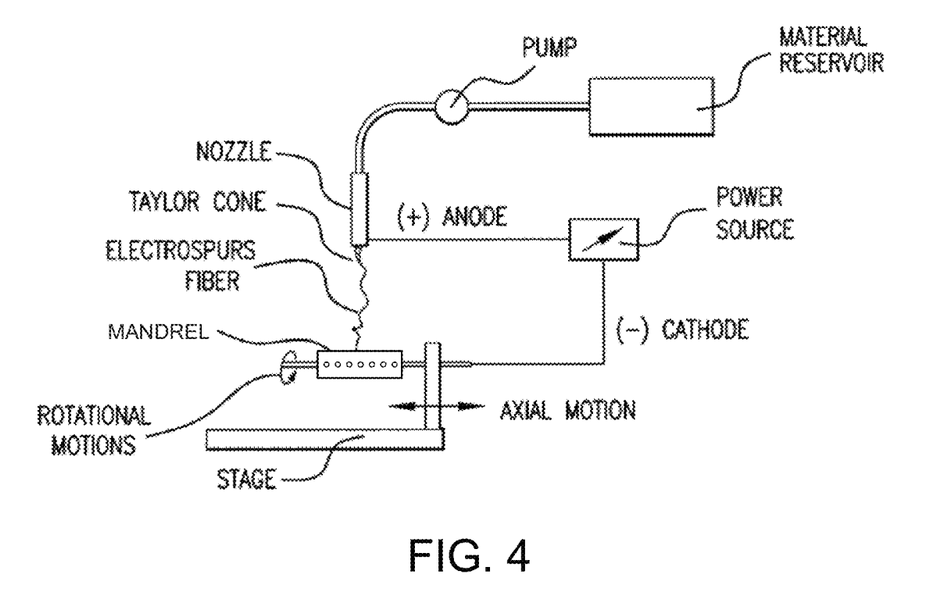

The e-spun polymeric member 14 is in fluid communication with the inflation lumen. The inflation lumen can supply fluid under pressure, and establish pressure, to the polymeric member for expansion in the blood vessel. As described below, in some embodiments, the expandable member 14 is used to treat a vessel wall via localized delivery of a therapeutic agent and in these embodiments, the inflation fluid can include a sclerosing agent to treat varicose veins, or other beneficial agent or medication to treat the vessel wall for other conditions, such as lesions, ischemia and the like. The e-spun polymeric member 14 can thus be inflated and deflated, and dispense medication Referring now to FIG. 3, electrospinning a polymer material is generally disclosed. The nozzle discharges electrospun material from a Taylor cone. The electrospun fiber is disposed on a inner mandrel to accumulate to form an e-spun polymeric member. Referring to FIG. 4, an exemplary apparatus is disclosed for fabricating the e-spun polymeric balloon. In one embodiment, an apparatus produces an electric field that guides a polymer material, such as a melt or fluid, extruded from nozzle to a charged mandrel. One end of a voltage source is electrically associated with the nozzle and the other end of the voltage source is electrically associated to the mandrel. The electric field created between the nozzle and the mandrel cause the polymer fluid or melt to overcome cohesive forces that hold the polymer solution together. For example and not limitation, the electric field strength may be between about 2,000 to 400,000 V/m. As a pump pushes the solution through the syringe/nozzle tip, a fluid jet of the polymer is drawn from the nozzle toward the mandrel by the electric field and dries during flight from the nozzle to the mandrel to form polymeric fibers on the body of the mandrel. In some embodiments, a rotating mechanism can be employed to rotate the nozzle and/or the mandrel. An angular rotation speed of 1,000 to 10,000 rpm can be used.

Figure 5:
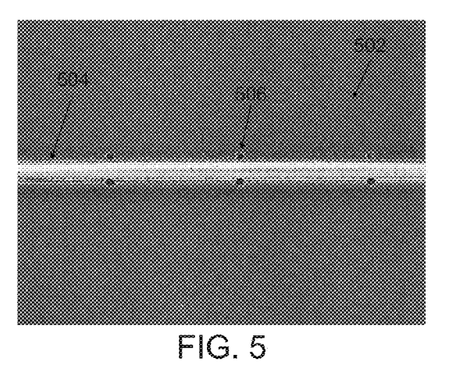
FIG. 5 is a view of an exemplary mandrel usable in combination with the electrospinning process depicted in FIG. 3.

In some embodiments, the mandrel has a profile that is approximately similar to the desired profile of the polymer balloon. Referring to FIG. 5, mandrel 502 comprises an elongate tubular body 504 having an outer surface and an inner surface to define a body wall. The body wall includes a plurality of openings 506 extending through tubular body wall 504. The openings 506 can be, for example, circular, oval or any other shape, as so desired. Each of the openings can be uniform in size, or alternatively, the openings can be configured so that they include openings of varied sizes. The diameter of the openings can range from 1 mm to 5 mm, however, openings 506 may be of any size, depending upon the intended use of the formed member. Additionally, the spacing of openings 506 on mandrel 502 may be varied. For example, openings 506 may be disposed uniformly along the entire length of the mandrel, or in a pattern/gradient of varying concentrations. In one embodiment, openings 506 are laterally spaced apart by 5 mm, and have a diameter of 0.005 inch, are axially distanced at about 120°. Alternatively, openings 506 may be solely disposed at a proximal end, a distal end, or centrally located on mandrel 502. However, any arrangement of openings 506 are contemplated. During the e-spinning process, fibers leave the positivity charged nozzle are accelerated toward the negatively charged target, in this case mandrel 502 with openings 506. The polymeric material will accumulate in the areas of highest density on the mandrel body. These areas of charge density are associated with areas of high conductivity. Thus, the body of the mandrel will have accumulated more espun polymer than will the less dense openings 506.

Figure 6:
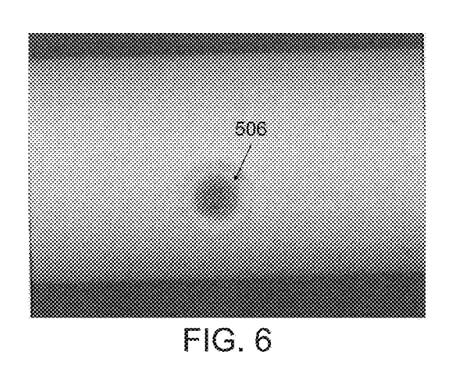
FIG. 6 is a view of the mandrel of FIG. 5 after electrospinning.

In one embodiment, the mandrel is grounded, and the fibers produced by the electrospinning are directed by the electric field toward the mandrel where the fibers are deposited and accumulated. As materials are electrospun onto the surface of mandrel 502 having openings 506, the area of the mandrel having openings 506 collects or accumulates less of the electrospun polymer compared to non porous sections of the tubular body 504. As a result, the electrospun member formed on the mandrel is configured with a polymeric wall having a varied thickness across a length. In other words, the areas of the balloon wall have a greater thickness than the area of the balloon wall corresponding to the mandrel openings 506, as depicted in FIG. 6. The areas of the balloon having less material because due to the manufacturing process with the mandrel with openings is suitable for delivering sclerotherapy agent or any other therapeutic agent through the more porous sections of the balloon.

In another embodiment, as described in U.S. Pat. No. 7,134,857, incorporated herein by reference in its entirety, mass produced e-spun polymers can be fabricated to form medical balloon 14. A rotatable spray head can include a reservoir holding polymeric fluid or melt to be dispensed or extruded and a plurality of nozzles. The rotatable spray head rotates about its center and polymeric material is dispensed from the nozzles. Furthermore, relative motion can be established between the spray head and expandable member 14 such that the spray head rotates and translates with respect to the expandable member 14. For example, the spray head can be translated while the expandable member 14 is rotated. An electric potential is applied to the rotatable spray head to establish an electrical field which extends to a collector mandrel constituting an opposite electrode. The electrospray medium upon extraction from the nozzle is guided along a direction of the electric field toward the mandrel that collects the electrospun material to form a medical device such as a balloon or stent, for example. In some embodiments, the mandrel can be positioned about 0.5 cm to 50 cm from the dispensing nozzle(s).

In other embodiments, other e-spinning processes can be used, for example, those described in U.S. Pat. Nos. 6,382,526 and 6,520,425, incorporated herein by reference in their entirety. In one embodiment, an electrospinning fixture is provided that includes a working stage for holding the mandrel for the electrospun polymer material. This stage may include rotational and axial movement capabilities and the motion of the stage can be controlled by a motor synchronized with a motor controller. The stage can include a holding fixture such as a chuck that accepts the mandrel and transmits motion thereto. The holding fixture can also be connected to a negative lead of a power source, making it the cathode of the electrolytic process. The positive lead of a power source is connected to the ejection nozzle, making the nozzle the anode of the electrolytic process. The nozzle can be connected to a reservoir of polymer material melted or dissolved in a solvent. A pump can be used to pump the polymer from the reservoir into the nozzle for electrospinning to the mandrel. Typically, electrospinning processes require high voltage but relatively low current. In one embodiment of the disclosed subject matter, the power source is capable of delivering 0 to 60 kilovolts of electrical potential, but generally operates in the range of 10 to 20 kilovolts during the electrospinning process. The current that is provided by the power source is generally in the 5 to 10 microampere range. It will be appreciated that these ranges can vary depending upon the electrospinning material and process parameters.

Figure 8:
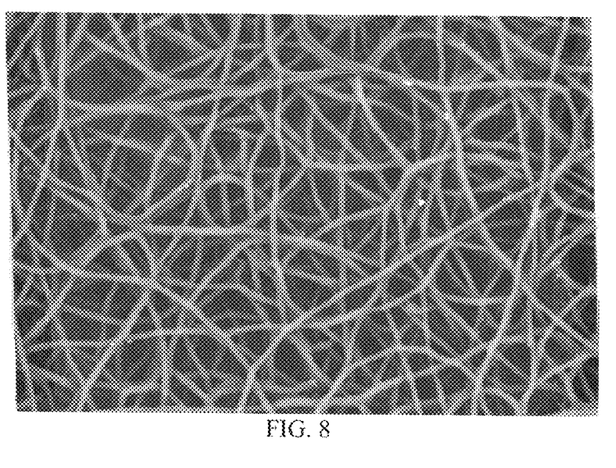
FIG. 8 is a view of the e-spun material of the expandable member in accordance with one embodiment of the described subject matter.
Figure 9:
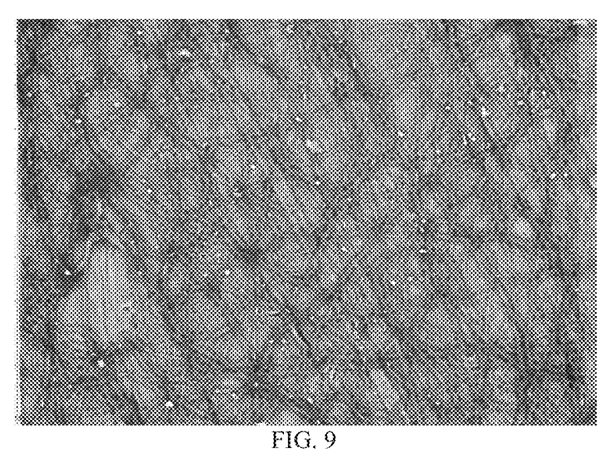
FIG. 9 is a view of the e-spun material of the expandable member in accordance with another embodiment of the described subject matter.

Various polymeric materials can be used for fabricating an e-spun medical balloon. For example, and not limitation, the electrospun fibers can be formed from polyurethane dissolved in a solvent such as acetone, polylactic acid (PLLA), tetrahydrofuran, N,N-dimethylformamide, chloroform, trifluoroethanol, hexafluoroisopropanol, or blends thereof. Other examples of polymers are described in *Structure Formation in Polymeric Fibers*, by D. Salem, Hanser Publishers, 2001, the entire contents of which are incorporated herein by reference. Depending on the type of solvent chosen, for example, the density of the fibers electrospun to make the polymeric member can be different. For example, referring to FIG. 8, a electrospun polymeric member formed from PLLA-PLC in HPIP 5% solvent is formed. As illustrated the fibers made from the electrospun process are elongate and form a porous web, whereas in FIG. 9, the PLA-PLC was in acetone and the web formed from the fibers have greater density.

Suitable organic or aqueous based electrospinning solvents, include but are not limited to, acetone, methyl ethyl ketone, cyclohexanone, dichloromethane, chloroform, trifluoroethanol, hexafluoroisopropanol (HFIP), tetrahydrofuran, N,N-dimethylformamide, ethyl acetate, isopropanol, ethanol, water or blends thereof. A particular embodiment of electrospinning material includes polyurethane dissolved in tetrahydrofuran, although this can be varied widely depending upon the requirements of the disclosed subject matter.

The nozzle can be located in a position that creates the desired electrospinning pattern. For example, if a random matrix pattern is desirable, the nozzle exit can be located greater than about 3 cm from the mandrel. If a more controlled pattern is desired, the nozzle can be located within about 3 cm from the mandrel surface.

The electrospinning fiber will normally be ejected from the nozzle adjacent to the anode toward the cathode. The fibers will preferably have diameters in the range of about 10 nanometer to 10 micrometer. Numerous parameters can be manipulated during the electrospinning process to achieve desired fiber characteristics and morphologies. For example, the applied voltage can be varied such that as the voltage is increased, the diameter of the fiber decreases. Conversely, the flow rate, viscosity (i.e. polymer concentration) and nozzle/outlet diameter can be increased to result in an increased fiber diameter. Also, as the solution conductivity, or distance between the nozzle and contact surface (e.g., mandrel, balloon) increases the fiber diameter will decrease. This range of fiber sizes will affect the gap size of the matrix since it will determine how much gap exists between overlapping fibers. The density of the fibers and the number of fiber layers will also affect the gap size. It is important to note that various changes to the electrospinning fibers can be made in accordance with this invention, which will affect the efficacy of the solution. For example, it is possible to electrospin a fiber that has two layers, a core (inner layer) and an outer coating (outer layer), by utilizing a specific capillary nozzle, as shown in FIG. 3. Likewise, a second coating (third layer) can be simultaneously spun, which can be a protective coating dissolvable in a solvent. Various methods and examples of electrospinning are described in U.S. Publication No. 2010/0081992, which is hereby incorporated by reference in its entirety.

To maximize fiber bonding and minimize layer delamination within the electrospun expandable member, fabrication distance can be lowered to an appropriate value to cause fibers to lightly bond between layers due to presence of more solvent with less evaporation distance. As is well know in the art, a shorter process distance results in wetter fibers and tighter junctions.

Further process variables such as polymer solution concentration as stated previously can also affect both morphology and fiber diameter. Increasing polymer concentration and solution viscosity while holding all other variables constant generally results in larger fiber diameter. Fiber diameters can then be varied from tens of nanometers to greater than a micron based on the parameters used. Wall thickness of the nanofiber expandable member could be controlled from tens of microns up to a millimeter or greater by adjusting fabrication time from a few minutes up to an hour or more. Fabrication parameters and material composition can also be optimized for each particular catheter delivery system, to allow for the desired radial force, flexibility and recoverability.

In accordance with another aspect of the disclosed subject matter, a sleeve or external sheath can be formed on the outer surface of the expandable member 104, e.g. balloon, via the electrospinning technique described herein. Additionally, the balloon 104 is inflated with a conductive fluid to improve the efficiency of the electrospinning process by shortening the spinning, time as well as provide a higher density coating as compared to electrospinning methods wherein the balloon is inflated only with air. For purposes of illustration and not limitation, examples of suitable conductive fluids include $KH_2PO_4$, $NaH_2PO_4$, NaCl or combinations thereof, though artisans of ordinary skill will also recognize that alternative conductive fluids are suitable. By employing this technique it is possible to form a sleeve with a 1 mm diameter on 1 mm balloon inflated with a conductive fluid. After which, the sleeve can be removed from the balloon and deposited over a coated and/or folded balloon for final assembly of the medical device.

The polymers dispensed from the electrospinning nozzle are conductive and the charged ions in the polymer solution are highly influential in jet formation. Thus, the ions increase the charge carrying capacity of the jet and create a higher tension with the applied electric field. In one embodiment, a 5% PLLA-PCL fiber in HFIP solvent was electrospun on a balloon inflated to 8 atmospheres with a solution comprising 25% of salt (NaCl) in distilled water for 25 cycles, or passes, which resulted in a sleeve thickness of 0.001 inch. To produce the same thickness sleeve via air-inflated techniques would require approximately 150 cycles, or passes of the nozzle. This demonstrates the effect the conductive-fluid inflation technique has on the efficiency of the electrospinning process, i.e., the conductive fluid increases the amount of charge transfer from the inner mandrel to the outer surface of the balloon. Consequently, an increase in the density of fibers deposited on the outer surface of the balloon is achieved, as compared to balloons inflated with air. This is believed to be due in part to the enhanced attraction forces which can produce a beadles fiber of smaller density than conventional air-inflated techniques. That is, as fibers leave the positively charged nozzle they are accelerated toward the negatively charged surface of the balloon, and will accumulate in areas of highest charge-density, which are in turn associated with areas of high conductivity. Conversely, with air-inflated spinning techniques, a layer of air is created between the conductive mandrel and the outer surface of the balloon. This layer of air acts as an insulator, which lowers the charge density on the surface of the balloon, resulting in a decrease of fiber coating that area. Thus, the conductive-fluid inflation medium provides greater control over the density, thickness, and location of deposited fibers in the electrospinning process.

In accordance with another embodiment, the fibrous matrix which is formed into an expandable balloon is formed from a melt-blowing or spunbonding process. The melt blowing process is well known in the art and involves extruding a fiber-forming thermoplastic polymer resin in molten form through orifices of a heated nozzle into a stream of hot gas to attenuate the molten resin as fibers which form a fiber stream, the fibers being collected on a receiver in the path of the fiber stream to form a nonwoven web. The fibrous web can then be shaped into an expandable member. A method for producing a melt-blown fibrous web is described in U.S. Pat. No. 3,978, 185 to Buntin et al., which is incorporated herein by reference in its entirety. The spunbonding process, equally well know in the art, is similar to the melt-blowing process, the two major differences between the two processes being i) the temperature and volume of the air used to attenuate the filaments and ii) the location where the filament draw or attenuation force is applied. A melt-blowing process uses large amounts of high-temperature air to attenuate the filaments. The air temperature is typically equal to or slightly greater than the melt temperature of the polymer. In contrast, the spunbonding process generally uses a smaller volume of air close to ambient temperature to first quench the fibers and then to attenuate the fibers. Methods for producing spunbonded webs are disclosed in U.S. Pat. No. 3,338,992 and U.S. Pat. No. 3,341,394 to Kinney; U.S. Pat. No. 3,276,944 to Levy; U.S. Pat. No. 3,502,538 to Peterson; U.S. Pat. Nos. 3,502,763 and 3,509,009 to Hartmann; U.S. Pat. No. 3,542,615 to Dobo et al. and U.S. Pat. No. 3,692,618 to Dorschner et al, the disclosures of which are incorporated herein by reference in their entirety. Both the melt-blowing and spunbonding processes can be used to produce fibers having a diameter of about 100 nanometers.

Polymers that are suitable for use in the melt-blowing and spunbonding processes which can be used to form the expandable structures include, but are not limited to polypropylene, polyethylene, polybutylene terephthalate, Nylon 6, Nylon 11, polycarbonate, polyurethanes, polyesters, poly(vinylidenefluoride) and poly(ester-amides).

During the electrospinning process, the solvent begins to evaporate. When the electrospinning fibers reach the mandrel surface, the remainder of the solvent evaporates leaving the electrospun fibers. As the electrospinning layers are added, additional crossing of the electrospinning fibers will result in a dense matrix of material having radial channels or gaps passing therethrough. The size and location of these channels and gaps can be controlled through various process parameters, such as solution composition, nozzle position, and other parameters known in the art. The apparatus and electrospinning process disclosed herein provide a protective matrix which is particularly suited for applications incorporating a therapeutic agent, e.g., a drug-coated balloon. For example, in some embodiments the electrospun fibers or conduit, can be applied directly to the mandrel and thereafter transferred to the expandable member 14. Additionally or alternatively, therapeutic-free fibers can be electrospun directly on the expandable member subassembly. In yet other embodiments, therapeutic loaded fibers can be electrospun onto the expandable member subassembly.

Once formed, the expandable member 14 can be attached to an elongated catheter shaft by any conventional and suitable techniques so as to be in fluid communication with an inflation lumen 20 as depicted in FIGS. 1, 2A and 2B. Similarly, the expandable member 14 can be folded or collapsed using known and suitable techniques for assembly, packaging, delivery and deployment as is known in the art.

Expandable member 14 can be utilized to treat various diseases or impairments, such as varicose veins. For example, if expandable member 14 is utilized to perform sclerotherapy, the inflation fluid can include a sclerosing agent, such as ethanol. For purpose of illustration and not limitation, Sclerosing agents compatible with the present invention include, but are not limited to, alcohols such as ethanol or polidocanol (POL), as well as sodium tetradecyl sulphate (STS), Sclerodex, hypertonic saline, glycerin and chromated glycerin, or combinations thereof. These sclerosing agents have been found to effect the cellular responses to growth stimulation and cause the vessel walls to immediately shrink upon exposure to the agents. While specific examples of sclerosing agents are described herein, it is to be understood that alternative therapeutic agents can be administered to the vessel wall utilizing the device and methods disclosed herein. Accordingly, as used herein, a "therapeutic agent" includes any agent that promotes health, recovery or diagnosis. For example, the therapeutic agent may be a drug, protein, or contrast agent.

Figure 7:
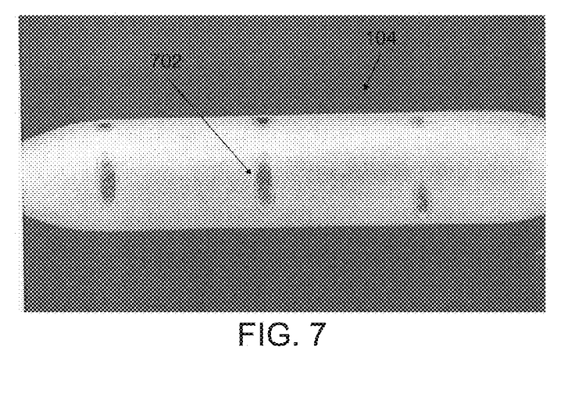
FIG. 7 is a view of the expandable member formed by the electrospinning process of FIG. 3.

As expandable member 14 is inflated, as depicted in FIG. 7, bumps or outward projections 702 form on the surface of expandable member 14 (e.g. when inflated at 100 Psi), which coincide with the location of holes 506 of the mandrel because these area have thinner walls. The thinner wall regions will also have a higher porosity than the surrounding wall regions, allowing for accurate delivery of the sclerosing agent to the wall of the varicose vein. As described above, the holes in the mandrel, and thus the resulting bumps or outward projections 702, can have a variety of sizes and/or shapes, as so desired. The different hole geometries provide different surface areas of porous material, which in turn provide different diffusion rates and/or amounts of the therapeutic agent. Furthermore, the different hole patterns allow for greater flexibility and customization in that varied hole densities can accommodate the needs of different patients and/or device applications. A further benefit of the existence of projections 702 is realized, when configured as a stent, in that the stent will resist the tendency of distorting or suffer from "dog-bone" effect. Instead, the stent will exhibit uniform expansion which in turn prevents changes in length or "foreshortening" as is common with conventional stent designs.

Figure 10:
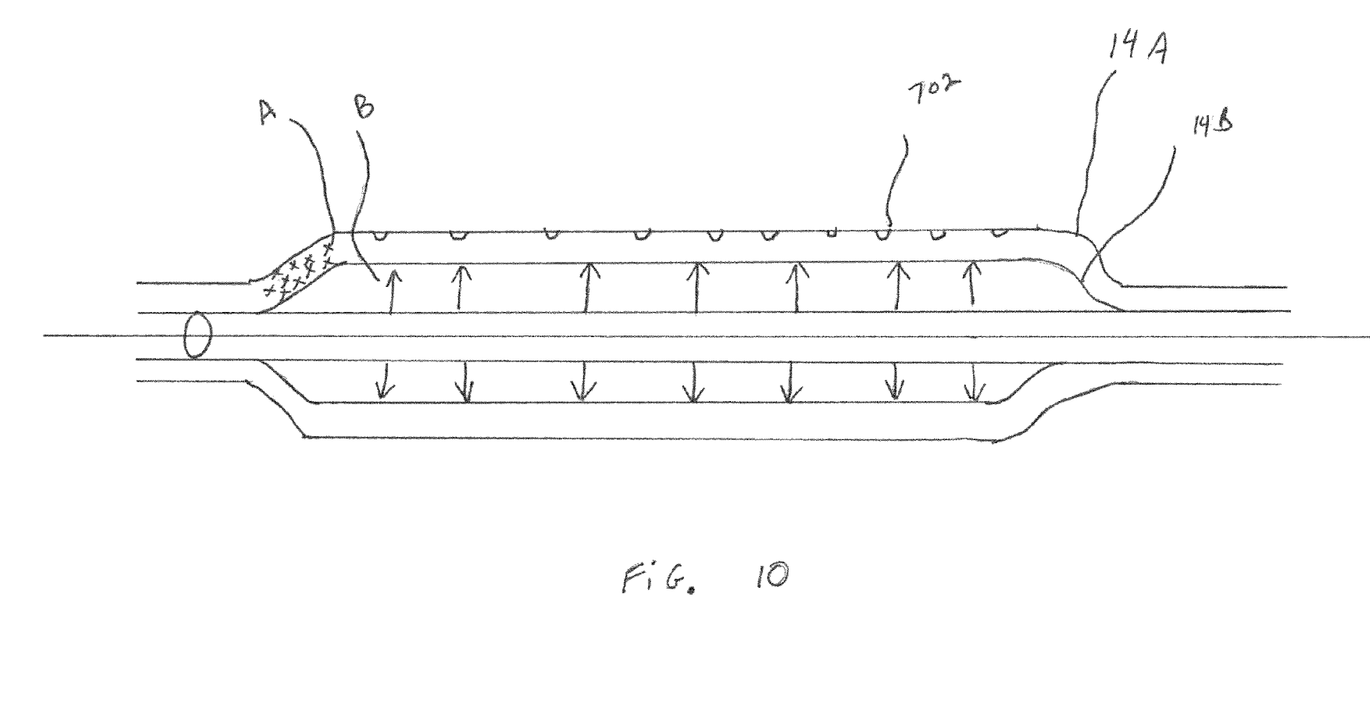
FIG. 10 is a view of an alternative embodiment in which the expandable member is configured as a dual or double balloon.

In another embodiment, the expandable member can be configured as a double balloon, as shown in FIG. 10. In this configuration two balloons are oriented in a coaxial relationship such that the inner balloon 14b is expanded, e.g. by inflation via air (shown as arrows B). Bumps or projections 702, as described above, are formed in the outer balloon 14a. In the expanded state, a therapeutic agent (shown as elements A) is provided between the exterior surface of the inner balloon 14b and the outer balloon 14a such that a desired amount of the agent is delivered through the projections 702.

In one embodiment, a method for treating a varicose vein is provided. The method includes delivering a catheter, having an e-spun polymeric member described above coupled at a distal end thereof, through an incision and into the varicose vein. Next the varicose vein is occluded, after which a sclerosing agent is dispensed from the porous wall sections of the e-spun polymeric member (e.g., balloon) to treat the varicose vein. In one embodiment, the sclerosing agent is dispensed proximal the occlusion such that the treated portion of the vein proximal of the occlusion is destroyed.

When the catheter 10, 10', 10" is introduced into the variscose vein, a source of sclerosing agent is coupled to the catheter lumen and operated (such as by a pump) to allow sclerosing agent to flow through the luminal space into the e-spun balloon 14 and out through the porous sections 506. The sclerosing agent dispensed from the porous section 506 with flow directly into the wall of the vein. The balloon 14 is moved along the length of the vein to dispense sclerosing agent along the length of the vein wall. The pressure exerted on the wall of the vein as the sclerosing agent is dispensed from the porous section 506 massages the sclerosing agent into the cells of the vein wall. When the entire length of the vein is treated, the occlusion site is de-occluded. After the treatment, the treated leg of the subject is preferably wrapped with a compression bandage.

Porous section 506 of the balloon 14 may be located on the proximal portion of the balloon, distal or intermediate portion of the balloon 14.

Example

A porous sleeve covered balloon was prepared by electrospinning processes. Materials: 5% PLLA-PLC 50:50 in HFIP solvent, 25% NaCl distilled in $H_2O$; Fl: 3.5 mm×20 mm PO2544; dental floss. A 25% salt solution was prepared and using an indeflator 20/20 a balloon was inflated to 8 ATM. While the balloon was inflated tight 10 cm from proximal balloon end with dental floss to keep balloon inflated during spinning Inflated balloon was positioned in spinning mandrel. Electrospinning was performed and volume and time for spinning balloon filled with conductive fluid was recorded and compared with e-spinning balloon filled with air. The results were that a sock was formed within only 25 passes versus 150 passes with air inflated balloon. Direct electrospinning is possible on inflated balloons via inflation with conductive solution. The liquid electrolyte methods is verified to be more efficient than using air to inflate the balloon.

As described above, the catheter of the disclosed subject matter can be used to deliver other types of intravascular medications or beneficial agents directly to the wall of a blood vessel and need not be limited to sclerotherapy or delivery of a sclerosing agent. Although the treatment of varicose veins generally involves treating the entire length of the vein, other treatments may require or prefer that only a selected portion of the blood vessel be treated.

While the above description focuses primarily on a medical device application of the disclosed subject matter, the techniques and apparatus disclosed herein have numerous alternative applications as well. For example, the electrospun fibers disclosed herein can be configured for use in a filtration system (for both gaseous and aqueous media). Here, electrospun fibers serve to remove bacteria and viruses during the manufacture of various pharmaceuticals. The superfine fibers ensure that molecules of unwanted, dangerous life forms do not pass through the solutions into the final product. Additionally, electrospun fibers can be employed as HEPA (High Efficiency Particle Accumulation) filters in vacuums, water purification and military applications.

Additionally, the electrospinning system disclosed herein is applicable in the textile industry for the development of protective clothing. The electrospinning process can be used to create fibers that incorporate anti-bacterial agents or compounds, such as oximes that break down nerve gases, insecticides, pesticides and other toxic compounds.

Another application of the electrospinning system disclosed herein in the medical device field is forming three dimensional porous biomedical scaffolds. Such devices can facilitate healing by providing a multitude of sides for cell and tissue growth and at the same time break down naturally in the body. As disclosed above, therapeutic agents can be incorporated in the fiber in such a way that the release or delivery rate of the agent is controlled by increasing the wall thickness of the electrospun fiber.

Furthermore, the electrospun fibers disclosed herein can be employed as long nanofiber reinforcements for composite structures. To increase the control of the orientation of the electrospun fibers, the polymer chains in the fibers can be cold drawn. Also, the electrospun fibers can be coated by chemical vapor deposition to enhance their properties. Some fibers can be coated with silver which serves as a disinfectant, if so desired. Metals, glasses and ceramics can be added to fibers via co-electrospinning, wherein different materials are pumped through two coaxially arranged chambers. This allows for spinning both hollow fibers as well as fibers having a core and a shell. Any number of layers can be formed, as so desired. Additionally, the electrospun fibers can include encapsulated nanoparticles.

Some additional applications of the disclosed subject matter include polymer batteries and fuel cells; interwoven electrodes and fabrics; genetically engineered collagen to serve as wound dressings and implants; coloring and waterproofing of fabrics; solar sails and mirrors for space applications;

While the disclosed subject matter is described herein in terms of certain preferred embodiments, those skilled in the art will recognize that various modifications and improvements may be made to the disclosed subject matter without departing from the scope thereof. Moreover, although individual features of one embodiment of the disclosed subject matter may be discussed herein or shown in the drawings of the one embodiment and not in other embodiments, it should be apparent that individual features of one embodiment may be combined with one or more features of another embodiment or features from a plurality of embodiments.

In addition to the specific embodiments claimed below, the disclosed subject matter is also directed to other embodiments having any other possible combination of the dependent features claimed below and those disclosed above. As such, the particular features presented in the dependent claims and disclosed above can be combined with each other in other manners within the scope of the disclosed subject matter such that the disclosed subject matter should be recognized as also specifically directed to other embodiments having any other possible combinations. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

What is claimed is:

1. A method of fabricating a medical balloon, comprising:
   charging a polymer material with an electric voltage;
   dispensing the charged polymeric material through a nozzle;
   collecting the charged polymeric material on a grounded mandrel, wherein the mandrel includes a tubular body having a plurality of openings extending through the tubular body, and
   forming a first electrospun inflatable medical balloon defined by a body having a varied thickness, and
   forming a second electrospun inflatable medical balloon, the first balloon disposed coaxially with respect to the second balloon.

2. The method of claim 1, wherein the varied thickness includes porous sections and non-porous sections.

3. The method of claim 1, wherein the method includes rotating the nozzle during the step of dispensing the polymeric material.

4. The method of claim 1, wherein the method includes rotating the mandrel during the step of dispensing the polymeric material.

5. The method of claim 1, wherein the electric charge applied to the polymeric material is between about 2000 to 400,000 V/m.

6. The method of claim 1, wherein the mandrel is positioned about 0.5 cm to about 25 cm from the nozzle.

7. The method of claim 1, further comprising electrifying a reservoir holding a polymer fluid.

8. The method of claim 1, wherein the nozzle is a taylor cone.

9. The method of claim 1, wherein the openings in the mandrel are between 1 micron and 1 cm.

* * * * *